(12) United States Patent
Stensrud et al.

(10) Patent No.: US 9,890,131 B2
(45) Date of Patent: Feb. 13, 2018

(54) DIRECT SYNTHESIS OF BIO-BASED ALKYL AND FURANIC DIOL ETHERS, ACETATES, ETHER-ACETATES, AND CARBONATES

(71) Applicant: ARCHER DANIELS MIDLAND COMPANY, Decatur, IL (US)

(72) Inventors: Kenneth Stensrud, Decatur, IL (US); Padmesh Venkitasubramanian, Forsyth, IL (US)

(73) Assignee: Archer Daniels Midland Company, Decatur, IL (US)

( * ) Notice: Subject to any disclaimer, the term of this patent is extended or adjusted under 35 U.S.C. 154(b) by 0 days.

(21) Appl. No.: 15/102,298

(22) PCT Filed: Dec. 19, 2014

(86) PCT No.: PCT/US2014/071512
§ 371 (c)(1),
(2) Date: Jun. 7, 2016

(87) PCT Pub. No.: WO2015/095710
PCT Pub. Date: Jun. 25, 2015

(65) Prior Publication Data
US 2017/0001971 A1    Jan. 5, 2017

Related U.S. Application Data

(60) Provisional application No. 61/918,795, filed on Dec. 20, 2013.

(51) Int. Cl.
C07C 67/08 (2006.01)
C07D 307/42 (2006.01)
(Continued)

(52) U.S. Cl.
CPC ............ C07D 307/42 (2013.01); C07C 67/08 (2013.01); C07C 67/343 (2013.01); C07C 68/06 (2013.01); C07D 307/12 (2013.01); C07D 493/04 (2013.01)

(58) Field of Classification Search
CPC .... C07D 307/42; C07D 307/12; C07C 67/08; C07C 67/343; C07C 68/06
(Continued)

(56) References Cited

U.S. PATENT DOCUMENTS 4,770,871 A * 9/1988 Greenshields ....... A61K 8/4973
424/464
4,997,843 A * 3/1991 Carceller ............. C07D 231/12
514/336
(Continued)

FOREIGN PATENT DOCUMENTS

CN    1128749    *  8/1996
CN    1554632    * 12/2004
(Continued)

OTHER PUBLICATIONS

Loupy; Tetrahedron 2002, 58, 1541-1549.*
(Continued)

Primary Examiner — Daniel R Carcanague
(74) Attorney, Agent, or Firm — William B. Miller

(57) ABSTRACT

A method of preparing a glycol mono-ether or mono-acetate, or carbonate involving either one of two pathways from alkylene glycols, HMF or its reduction derivative products (i.e., FDM, bHMTHFs), is provided. In particular, according to one pathway, the alkylene glycol, HMF or FDM, bHMTHFs are reacted with a dialkyl carbonate in the presence of a deprotonating agent, in substantial absence of an extrinsic catalyst, to produce an ether, and subsequently reacting the ether with an acid base. According to the other
(Continued)

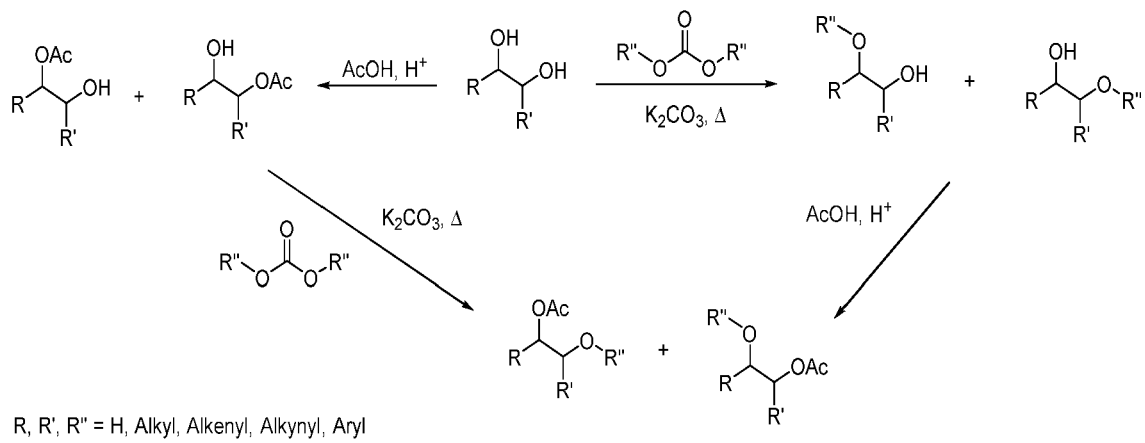

R, R', R" = H, Alkyl, Alkenyl, Alkynyl, Aryl pathway, alkylene glycols are reacted with an acetate donor in the presence of an acid, base, to generate an alkylene mono-acetate, and etherified with a carbonate in the presence of a deprotonating agent.

8 Claims, 3 Drawing Sheets

(51) Int. Cl.
  *C07D 493/04* (2006.01)
  *C07C 67/343* (2006.01)
  *C07C 68/06* (2006.01)
  *C07D 307/12* (2006.01)

(58) Field of Classification Search
  USPC .......................................................... 549/500
  See application file for complete search history.

(56) References Cited

U.S. PATENT DOCUMENTS

| | | | | |
|---|---|---|---|---|
| 5,849,955 | A | * | 12/1998 | Notari ..................... C07C 45/71 568/315 |
| 6,794,547 | B2 | * | 9/2004 | Borredon ................. C07C 41/16 568/628 |
| 2004/0232383 | A1 | * | 11/2004 | Imamoto ............... C07D 493/04 252/299.7 |
| 2008/0182831 | A1 | * | 7/2008 | Biggadike ............ C07J 41/0094 514/177 |
| 2009/0253920 | A1 | * | 10/2009 | Sanborn ............... C07D 493/04 549/464 |

FOREIGN PATENT DOCUMENTS

| | | | |
|---|---|---|---|
| CN | 101475469 | * | 7/2009 |
| WO | WO 2007089455 | * | 8/2007 |
| WO | WO 2013121190 | * | 8/2013 |
| WO | WO2016099789 | * | 6/2016 |

OTHER PUBLICATIONS

Tundo; Acc. Chem. Res. 2002, 35, 706-716.*
Shaikh;Tetrahedron 2007, 63, 3380-3388.*
Abenhaim; Carbohydrate Research 1994, 261, 255-266.*
Weidlich; Green Chemistry Letters and Reviews, 2007, 11, 53-59.*
Liang; New J. Chem., 2010, 34, 2534-2536.*

* cited by examiner

R, R', R" = H, Alkyl, Alkenyl, Alkynyl, Aryl

R ≥ C3, allyl, benzyl, aryl

R ≥ C3, allyl, benzyl, aryl

R ≥ C3, allyl, benzyl, aryl

DIRECT SYNTHESIS OF BIO-BASED ALKYL AND FURANIC DIOL ETHERS, ACETATES, ETHER-ACETATES, AND CARBONATES

BENEFIT OF PRIORITY

The present application is a 371 National Phase Entry of International Application No. PCT/US 2014/071512, filed Dec. 19, 2014, which claims priority to U.S. Provisional Application No. 61/918,795, filed on Dec. 20, 2013, the contents of each are incorporated herein by reference.

FIELD OF INVENTION

The present invention relates to a method for converting biologically-derived glycols into useful products. In particular, the invention pertains to a simple and green process of synthesizing a variety of compounds from alkylene glycols or furanic diols.

BACKGROUND

Having both an ether and alcohol functional group in the same molecule, glycol ethers are one of the most versatile classes of organic solvents. These molecules combine the best solvency features of alcohols and ethers, which allows for good miscibility and solvency in a wide range of organic chemicals and oils, as well as solubility in water. Glycol ethers also have higher boiling points. For these reasons, glycol ethers are prominent in the (i) surface coating industry as active solvents for resins, (ii) brake fluid industry as solvents, (iii) petroleum industry as anti-icers in various petroleum based fuels, (iv) automotive industry as anti-freezes, and (v) specialty products for use in household goods.

Typically, glycol ethers are labeled either "e-series" or "p-series" glycol ethers, depending on whether they are made from ethylene or propylene, respectively. Typically, e-series glycol ethers are found in pharmaceuticals, sunscreens, cosmetics, inks, dyes and water based paints, while p-series glycol ethers are used in degreasers, cleaners, aerosol paints and adhesives. E-series glycol ethers are higher in molecular weights, and can be used as intermediates that undergo further chemical reactions. P-series glycol ethers are generally high performance industrial solvents.

The preparation of glycol ethers has conventionally involved the generation of an alkylene oxide. For instance, one can react ethylene oxide (EO) or propylene oxide (PO) with alcohols in the e-series and p-series respectively. The glycol ether molecules can contain one or more EO or PO molecule in them. Typical alcohols used include methanol, ethanol, propanol, butanols, pentanols and hexanols. This reaction can produce glycol ethers of varying chain length depending on the molar ratio of reactions and temperature and pressures used in the reaction. Milder conditions and lower molar ratios of the alkylene oxide to alcohol will produce the monoalkylene glycyl ethers, while using more alkylene oxide and higher temperatures and pressures produce the di- and tri-alkylene glycol ethers. The products are purified by distillation. Glycol ethers can then be further reacted (esterified) with acetic acid to produce the corresponding acetate ester products. Hence, a whole family of products with multiple possible combinations exists. (See generally, e.g., Henry Chinn et al., "Marketing Research Report: Glycol Ethers," CHEMICAL ECONOMICS HANDBOOK, 663.5000A-633.5005Q (November 2010), SRI Consulting.)

Alternatively, the alkylene oxide can be synthesized by hydration of the alkylene with hypochlorous acid followed by base catalyzed epoxidation or by direct epoxidation of the alkylene with t-butyl hydroperoxide.

In another process, glycol ethers can be produced by the reaction of an alcohol with an olefin oxide in the presence of an acidic or basic catalyst. For instance, U.S. Pat. No. 6,124,506, describes an another process of glycol ether synthesis which involves reacting an olefin oxide with an alcohol over a catalyst comprising a layered double hydroxide (LDH) clay with its layered structure intact and having interlamellar anions, at least some of which are metal anions or (poly)oxometallate anions. In a similar fashion, U.S. Pat. No. 8,748,635 B2, describes a method for the preparation of anhydrosugar ethers by alkylation of anyhydrosugar alcohols using a solid phase zeolite catalyst.

Alkylene glycols can be generated by diverse processes. For instance, in one pathway, one subjects glucose to hydrogenation and hydrogenolysis to generate propylene glycol (PG) or ethylene glycol (EG). In another pathway, one ferments glucose to produce ethanol and $CO_2$. Ethanol is then converted to ethylene oxide with a silver catalyst, which then reacts with $CO_2$ to form cyclic ethylene carbonate, which generates a corresponding dialkyl carbonate when reacted with an alcohol. In the dehydration/reduction step to make epoxides one requires an additional reaction step. These processes all involve multiple steps that both add to the complexity and costs of producing the desired product.

Commercial manufacturers desire a simpler, single step etherification process. The currently available processes for synthesis, however, do not enabled one to make ethers directly from alkylene glycols (e.g., ethylene glycol (EG) and propylene glycol (PG)) derived from bio-based resources. Several preceding or intervening steps must first take place. At present, no process is known that can selectively make bio-based alkylene glycols into respective mono-ethers directly without oxidization. Hence, a new process that provides a route for direct etherification of not only alkylene glycols but also cyclic (furanic) diols as starting materials would be a welcomed advance.

SUMMARY OF THE INVENTION

The present disclosure relates to a method of preparing a mono-ether from a diol compound, comprising either a first pathway or second pathway. In the first pathway, the diol compound contacts an $R^1$ organic acid in the presence of a Brønsted acid at a temperature and for time sufficient to form a $R^1$ mono ester of the diol compound, then the $R^1$ mono ester of the diol compound contacts a $R^2$ alkyl diester of the formula $R^2(CO_3)R^2$ in the presence of a deprotonating agent at a temperature and for a time sufficient to form the monoester ether. In the second pathway, the diol compound contacts the an $R^2$ alkyl diester of the formula $R^2(CO_3)R^2$ in the presence of a deprotonating agent at a temperature and for a time sufficient to form a mono ester of the diol compound, then the mono ester of the diol compound contacts an $R^1$ organic acid in the presence of a Brønsted acid at a temperature and for time sufficient to form the monoester ether. The $R^1$ and $R^2$ are either the same or different alkyl, cyclo-alkyl or aromatic moieties.

Additional features and advantages of the present process will be disclosed in the following detailed description. It is understood that both the foregoing summary and the following detailed description and examples are merely representative of the invention, and are intended to provide an overview for understanding the invention as claimed.

DETAILED DESCRIPTION OF THE INVENTION

Section I.—Description

A.

The present synthesis method provides a simple, clean and elegant process for preparing ethers and/or acetates directly from alkyl or furanic diols without need to either dehydrate or reduce the starting materials from renewable, bio-based materials. In contrast to the often complex and harsh conditions of conventional ether synthesis, the present method involves reacting an alkyl glycol with a solution of a dialkyl-carbonate reagent in the presence of a deprotonating agent, and in substantial absence of any other extrinsic catalyst. As used herein, the term "substantial absence" refers to a condition in which an extrinsic catalyst is either largely or completely absent, or is present in de minimis or trace amount of less than catalytic efficacy. In other words, no extrinsic catalyst is present, or is present at a level less than 5%, 3%, or 1% weight/weight relative to the amount of dialkyl-carbonate reagent in the reaction.

The method can be used to make mono-ethers, mono-esters, and alkoxy-esters from renewable alkylene, alkyl or furanic diols without need to either oxidize to form oxides or dehydrate and reduce to form epoxides. Examples of diols are glycols such as ethylene glycol (EG), propylene glycol (PG), and 2,3-butane diol (BDO). Alternatively, the reactant materials may be ethylene glycol mono-acetate, propylene glycol mono-acetate, or a mixture thereof. The furanic diol reactant can be the reduced analogs of HMF—furan-2,-5-dimethanol (FDM), and/or 2,5-bis-hydroxymethyl-tetrahydro-furan (bHMTHF). Alternatively, one may etherify or acetylate HMF itself when it is the reactant under the present reaction conditions.

Generally according to the present method, glycol mono-ethers are synthesized according to a base-mediated process. According to an embodiment, mono-acetates, or ether-acetates or glycol, mono- or dicarbonates are prepared directly from alkylene glycol precursors in a simple, direct fashion using alkyl-carbonate as an alkylating agent and/or acid-catalyzed Fischer acetylation. In another embodiment, the method also enables one to selectively prepare ethers, acetates, aggregate ether-acetates, mono-carbonates and di-carbonates from furanic diols. According to certain embodiments, the mono-ether is the favored and predominant product resulting from the reaction.

Figure 1:
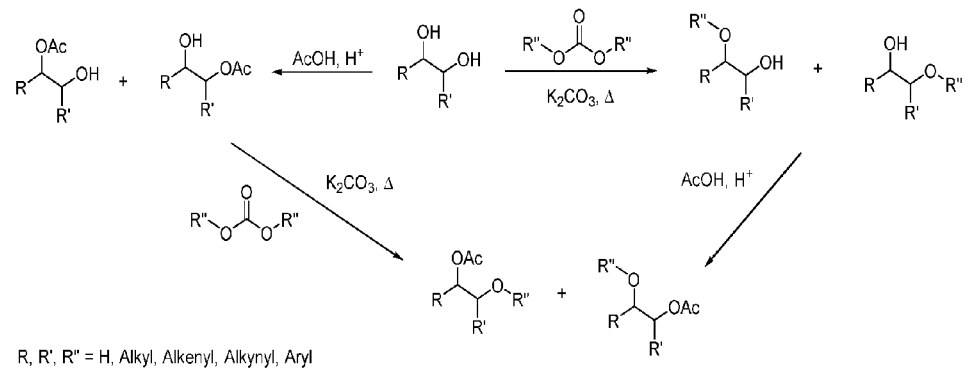
FIG. 1 is a general schematic showing two synthesis pathways in preparing etherified or acetylated diols from an alkylene diol.

FIG. 1 represents a schematic of two alternate pathways according to the present invention for preparing a glycol mono-ether or mono-acetate ester. Both pathways will enable one to generate either ether or acetate products. In the first pathway, one reacts either an alkylene glycol with a solution of a dicarbonate reagent in the presence of a deprotonating agent, in substantial absence of an extrinsic catalyst, to produce an ether, and subsequently acetylating the ether with an acid, base or enzymatic catalyst. In the second pathway, one reacts the alkylene glycol with an acetate donor in the presence of an acid, base, or enzymatic catalyst to generate an alkylene mono-acetate, and then etherifying with a carbonate in the presence of a deprotonating agent or base. In a subsequent step, one reacts an ether product of the first pathway or acetate product of the second pathway with a carbonate containing $C_3$ chains or higher, allyl, phenyl, or benzyl, to produce a mono-carbonate or dicarbonate or both.

Thus, when starting with an alkylene glycol according to the first pathway, one will generate an ether in a first step. Alternatively, one will make an acetate in the first step in the other second pathway. In particular, according to the first pathway, the alkylene glycol contacts a dialkylcarbonate reagent in the presence of a deprotonating agent in substantial absence of an extrinsic catalyst to produce ethers. Subsequently, one acetylates the ether product with either an acid (e.g., acetic acid) as shown, or alternatively with a base (e.g., any alkoxide base—methoxide), or enzymatic catalyst. According to the second pathway, alkylene glycols are reacted with an acetate donor (e.g., free acid, anhydride, ether) in the presence of a mineral acid (alternatively a base or enzymatic catalyst) to generate an alkylene mono-acetate, which is then etherified with a carbonate in the presence of a deprotonating agent or base. In a following step, the intermediate ether or acetate product is, respectively, acetylated or etherified to a final product.

The dialkyl-carbonate reagent can have an R-group with 1 to 20 carbon atoms. When the R-group is a methyl, ethyl, propyl group, an ether is usually the product of the reaction. When the R-group is a $C_4$-$C_{20}$ group a mono-alkylcarbonate is generated. The larger or more bulky R-moiety tends to promote the formation of a mono-alkylcarbonates. When the etherifying agent contains an R-group that is an allyl, phenyl, or benzyl moiety or has $C_4$ or greater chain, the product tends to be a mono- or dialkyl-carbonate or a mixture of both.

In other embodiments, the present method reacts directly an alkyl or furanic diol or glycol acetate with an alkyl carbonate in the presence of a weak base (e.g., pKa=8-11), to generate corresponding mono or di-ether compound if the carbonates have alkyl R-groups of less than or equal to about 3 carbons.

The reaction is assisted by a deprotonating agent or a proton acceptor such as a Brønsted base. Various proton acceptors may include, for example, at least one of the following: calcium, potassium or sodium carbonate, an amine, ammonia, etc. The mineral carbonates, in particular, exhibit low solubility in the reactor medium, which makes the carbonates easier to separate from the final products in downstream processing.

The pathways can be inverted, i.e., the glycol can be mono-acetylated first, then etherified in the aforementioned manner. The etherification occurs without an extrinsic catalyst, but by merely deploying a Brønsted base to facilitate the alkylation. The Brønsted base has a pKa of at least 4, which assists the —OH deprotonatation of the polyol.

The amount of dialkyl-carbonate reagent employed in the reaction can be in an amount of at least one (1) to about three (3) stoichiometric equivalents per alkylene glycol molecule. For the preparation of a mono-ether the amount of dialkyl-carbonate reagent is present at about two (2) stoichiometric equivalents per hydroxyl (OH) group of the alkyl diol.

In certain embodiments, the carbonate reagent can be one of the functional groups: mono-propyl, mono-butyl, mono-pentyl, mono-hexyl, mono-benzyl, mono-phenyl, mono-allyl, di-propyl, di-butyl, di-pentyl di-hexyl, di-benzyl, di-phenyl, di-allyl. The resulting ether or carbonate product, respectively, can be either: a mono-alkyl, ether or dialkyl ether, or mono-alkyl, mono-allyl, mono-aryl carbonate, or dialkyl, diallyl, or diaryl carbonate.

In another aspect, the present disclosure pertains to the ethers, acetates and alkyl-carbonates synthesized according the foregoing method. In general, the mono-ether of the alkylene glycol compound is at least one of the following: mono-ether of ethylene glycol (EG), propylene glycol (PG), or 2,3-butanediol (BDO). The mono-acetate of the alkylene glycol compound is at least one of the following: ethylene glycol, propylene glycol mono-acetate, or 2,3-butane-diol (BDO).

In general, the acetate of the alkylene glycol compound is at least one of the following: ethylene glycol (EG), propylene glycol (PG), 2,3-butanediol (BDO), ethylene glycol mono-ether, or propylene glycol mono-ether, 2,3-butanediol respectively.

In general, the mono- or dialkyl-carbonate product can contain at least one of the following: alkyl, allyl or aryl groups: a mono-butyl, mono-pentyl, mono-hexyl, mono-benzyl, mono-phenyl, mono-allyl, di-butyl, di-pentyl, dihexyl, di-benzyl, di-phenyl, di-allyl, or a mono- or di-alkyl group from $C_3$-$C_{20}$ carbon atoms.

B.

Figure 2:
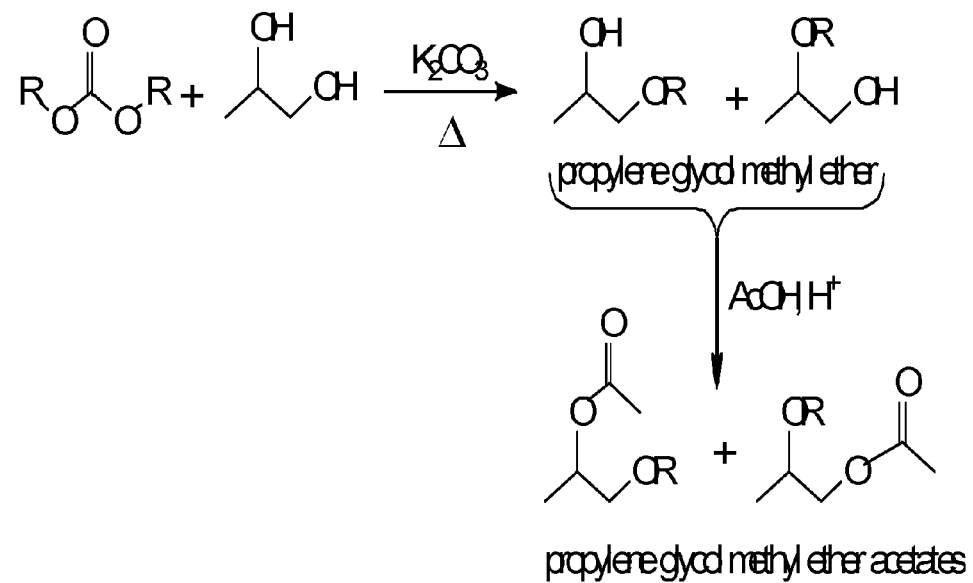
FIG. 2 is a schematic of a reaction according to an embodiment of the present method, which shows propylene glycol and propylene glycol-acetate alkyl etherification.

A synthesis according to an embodiment of the present method is illustrated in FIG. 2. As shown in this embodiment, the propylene glycol reacts with a dicarbonate under heat and in the presence of a nucleophile, such as potassium carbonate, to generate propylene glycol alkyl ethers.

Figure 3:
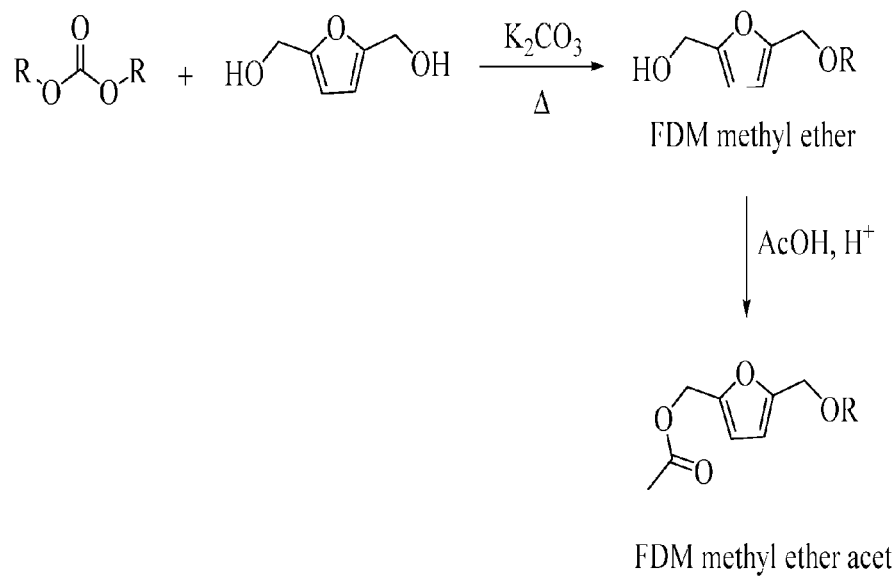
FIG. 3 is a schematic of a reaction according to another embodiment of the present method, which shows FDM and FDM acetate alkyl etherification.
Figure 4:
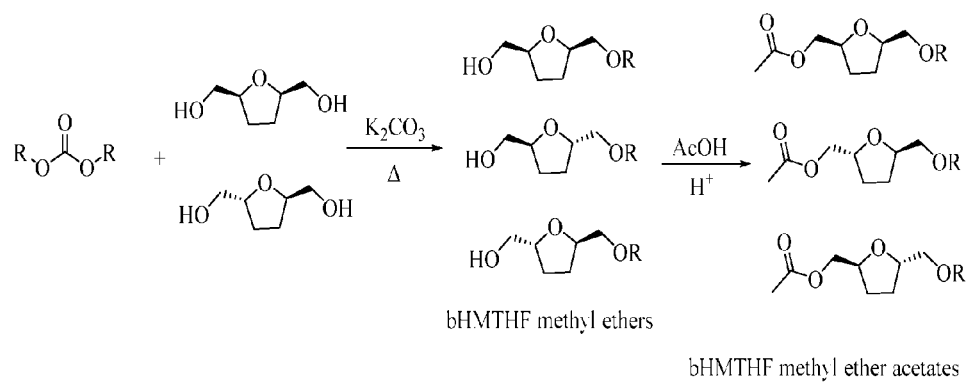
FIG. 4 is a schematic of a reaction according to an alternate embodiment of the present method, which shows bHMTHFs and alkyl etherification of bHMTHF acetates.

These ethers can further be processed to make propylene glycol alkyl ether acetates by treating with an acetyl-alcohol and acid. Similarly, the alkylation reactions depicted in FIGS. 3 and 4, show alternate embodiments using furanic diols, FDM and bHMTHFs, respectively. In FIG. 3, FDM reacts with dialkyl-carbonate to produce FDM alkyl ether, which is subsequently converted to FDM alkyl ether-acetate. In FIG. 4, two bHMTHF isomers are converted to three bHMTHF alkyl ether isomers by reacting with ethanol and an acid catalyst, and subsequently to three bHMTHF alkyl ether acetate isomers after acid treatment with acetic acid.

An advantage of the present methods is that they can provide simple, clean and elegant processes for preparing ethers directly from an alkylene glycol, in particular a biologically-derived alkylene glycol. As used herein the terms "biologically-derived" or "bio-based" refer to hydrocarbon molecules produced from renewable biological resources such as plants, cellulosic, or agricultural biomass or derivatives thereof, in contrast to so-called fossil-based or petroleum-based hydrocarbons. The clean process can help to simplify downstream separation and purification processes.

According to an embodiment, when the etherification is conducted neat in dialkyl carbonate, the dialkyl ether analog is the only product observed. When the etherification is conducted with about one equivalent of dialkylcarbonate (i.e., a stoichiometric amount of alkylating agent) only monoether products are generated, although in relatively low yields (e.g., ≤10%). Most of the propylene glycol or ethylene glycol remains unreacted. Optimization of the conditions, however, can improve target yields. Improved yields of target monoalkyl ethers, for instance, can be achieved using about two or three equivalents of dialkyl-carbonate and modifying other reaction parameters such as a lower temperature or longer reaction time.

The method provides an environmentally benign approach for etherification of the glycols, according to a controlled reaction performed under relatively mild temperature and ambient pressure. The reaction is performed generally at a temperature between about 70° C. and 150° C. Typically, the reaction is at a temperature in the range of about 70° C. or 80° C. to about 130° C. or 140° C. More typically, the reaction temperature is in a range from about 80° C. or 90° C. to about 110° C. or 120° C. (In most reactions, the temperature is under about 125° C. These mild reaction conditions help to control and minimize the formation of byproduct compounds or other potential isomers and impurities.

If the present etherification reactions are operated at higher temperatures, such as about 130° C. to about 150° C. for prolonged reaction times of about 24 or 40 hours, then one can produce significant yields of the ether product with a relatively high selectivity and level of purity.

C.

1. Alkylene Glycol Etherification

One can adapt the general synthesis process as described herein to make a variety of common glycol ethers. For instance, Table 1 lists some common, industrially useful glycol ethers along with their abbreviations and chemical names.

TABLE 1

| Common Name | Abbreviation | Chemical Name |
|---|---|---|
| ethylene glycol monomethyl ether | EGME | 2-methoxyethanol |
| ethylene glycol monomethyl ether acetate | EGMEA | 2-methoxyethyl acetate |
| ethylene glycol monoethyl ether | EGEE | 2-ethoxyethanol |
| ethylene glycol monoethyl ether acetate | EGEEA | 2-ethoxyethyl acetate |
| ethylene glycol monopropyl ether | EGPE | 2-propoxyethanol |
| ethylene glycol monobutyl ether | EGBE | 2-butoxyethanol |

TABLE 1-continued

| Common Name | Abbreviation | Chemical Name |
|---|---|---|
| ethylene glycol dimethyl ether | EGDME | 1,2-dimethoxyethane |
| ethylene glycol diethyl ether | EGDEE | 1,2-diethoxyethane |
| diethylene glycol | DEG | |
| diethylene glycol monomethyl ether | DEGME | 2-(2-methoxyethoxy) |
| ethanol diethylene glycol monoethyl ether | DEGEE | 2-(2-ethoxyethoxy) ethanol |
| diethylene glycol monobutyl ether | DEGBE | 2-(2-butoxyethoxy) ethanol |
| diethylene glycol dimethyl ether | DEGDME | bis(2-methoxyethyl) ether |
| triethylene glycol dimethyl ether | TEGDME | |
| propylene glycol monomethyl ether | PGME | 1-methoxy-2-propanol |
| propylene glycol monomethyl ether acetate | PGMEA | |
| dipropylene glycol | DPG | |
| dipropylene glycol monomethyl ether | DPGME | |

2. Furanic Etherification

The present reactions can also be employed with furanic compounds. FIG. 3 shows a schematic of a synthesis reaction according to an embodiment in which a FDM is reacted with dialkyl-carbonate to form a FDM mono-alkyl-ether. Subsequently, the ether is acetylated to generate the corresponding FDM alkyl-ether-acetate. FIG. 4 depicts a similar two-step reaction with bHMTHFs (THF-diols), where bHMTHF is converted to the corresponding THF alkyl ethers and then acetylated to the THF alkyl ether-acetates.

In general, the furanic diol is at least one of the following: FDM, bHMTHF diestereomers, respectively; FDM-mono-acetate, bHMTHF-mono-acetate diestereomers, respectively. The ether product has at least one of the following alkyl groups: a mono-alkyl, mono-ethyl, mono-allyl.

3. Alkyl-Carbonate Formation

In another aspect, the present reactions are adaptable to make organo-carbonates, which are a class of reactive platforms with diverse utilities, particularly in trans-esterifications, alkylations, or arylations.

Figure 5:
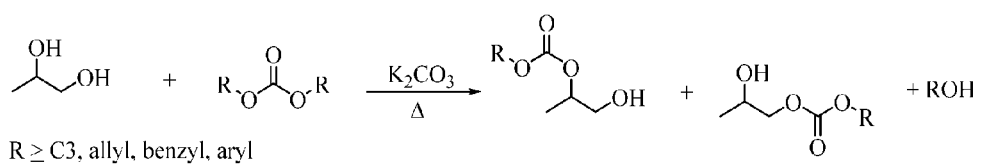
FIG. 5 is a schematic of a reaction according to another embodiment of the present method, which exhibits the synthesis of alkylene glycol carbonates.
Figure 6:
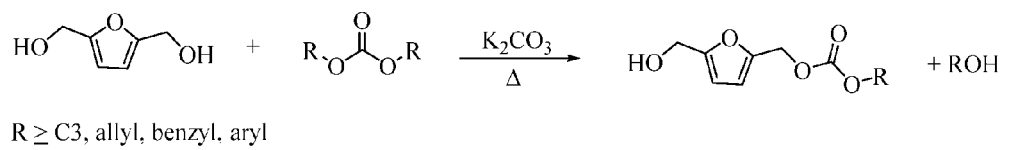
FIG. 6 is a schematic of a reaction according to another embodiment of the present method, which reveals the synthesis of FDM carbonates
Figure 7:
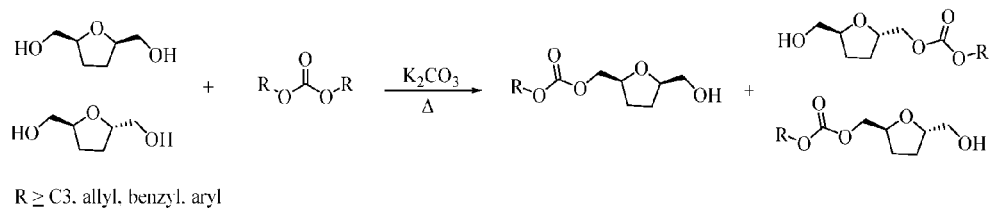
FIG. 7 is a schematic of a reaction according to another embodiment of the present method, which demonstrates the synthesis of bHMTHF carbonates.

FIGS. 5-7 represent three separate generic reactions for preparation of carbonates according to different embodiments, when the R-group of the dialkylcarbonate reagent is $C_3$ or greater, allyl, benzyl, or aryl. In FIG. 5, propylene glycol is converted to a corresponding diaklokycarbonate. In FIG. 6, FDM is converted to a furan carbonate, and in FIG. 7, bHMTHFs are converted to isomeric THF carbonates.

Section II.—Examples

The following examples are provided as further illustration of the synthesis of ethers from propylene glycol and ethylene glycol, and other aspects of the present disclosure. Changes in parameters and conditions (e.g., changes of temperature, time and reagent concentrations, and particular starting species and catalysts and amounts thereof) can affect and extend the full practice of the invention.

A. Glycol Mono-Acetates

The following examples illustrate reaction for synthesizing propylene glycol mono-acetate. Glycol acetates constitute materials that are useful in applications, such as solvents, precursors for additives, binders, plasticizers, lubricants and surfactants.

Example 1: Synthesis of Propylene Glycol Mono Acetate

A 500 mL round bottom flask equipped with dean stark apparatus was charged with 100 g of propylene glycol, 75 g of acetic acid and 5 g of a macroporous polymer catalyst (known commercially as Amberlyst™ 70 from Dow Chemical, Inc.) for use in high-temperature heterogeneous catalysis. The reaction mixture is heated to 120° C. and water was removed from the reaction mixture. The residue contained mostly propylene glycol mono-acetate.

Example 2: Synthesis of Propylene Glycol Mono Acetate

A 500 mL round bottom flask equipped with dean stark apparatus was charged with 100 g of propylene glycol, 115 g of ethyl acetate and 0.5 g of sodium methoxide. The reaction mixture was heated to 90° C. and ethanol was removed from the reaction mixture. The residue contained mostly propylene glycol mono-acetate.

Example 3: Synthesis of Propylene Glycol Mono Acetate

A 1 L autoclave engineer reactor was charged with 200 g of propylene glycol, 150 mL of acetic acid and 2 drops of Conc. $H_2SO_4$. The reactor body was assembled and the reactor was heated to 130° C. for 3 h. The reactor was cooled. The product consisted mostly of propylene glycol mono-acetate.

B. Linear Alkylene Glycol Mono-Ethers

Example 1: PG Methyl Etherification in Methanol (1:1 PG/DMC)

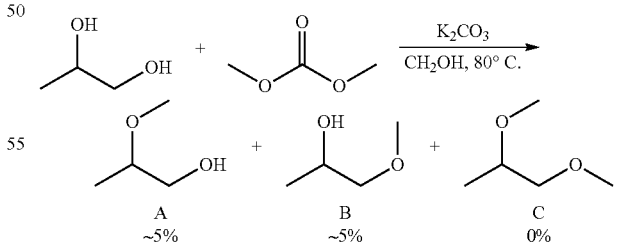

Experimental:

A 100 mL boiling flask was charged with 5 g of propylene glycol (PG, 65.7 mmol), 5.53 mL of dimethyl carbonate (65.7 mmol), 18.2 g of potassium carbonate, and 40 mL of methanol. The mixture was equipped with a Friedrichs condenser and refluxed (~80° C.) overnight. After this time, the heterogeneous mixture was cooled to room temperature, excess potassium carbonate filtered, and filtrate stored. A sample of the filtrate was submitted for quantitative analysis, the results of which indicated that approximately 10% of PG had converted evenly to the corresponding mono-methyl ethers A and B. Neither the PG dimethyl ether nor other products were described.

Example 2: PG Methyl Etherification in Methanol (1:2 PG/DMC)

Experimental:

Similar to the reaction described in Example 1, greater amount of methyl ether was produced in another reaction in which the ratio of propylene glycol and diemethyl carbonate was at a 1:2. A 100 mL boiling flask was charged with 5 g of propylene glycol (PG, 65.7 mmol), 11.06 mL of dimethyl carbonate (131.4 mmol), 18.2 g of potassium carbonate, and 40 mL of methanol. The mixture was equipped with a Freidrichs condenser and refluxed (~80° C.) overnight. After this time, the heterogeneous mixture was cooled to room temperature, excess potassium carbonate filtered, and filtrate stored. A sample of the filtrate was quantitatively analyzed by GC/MS, the results of which indicated that approximately 40% of PG had converted evenly to the corresponding mono-methyl ethers (18% A and 18% B) with approximately 4% conversion to dimethyl ether.

Example 3: PG Methyl Etherification, Neat

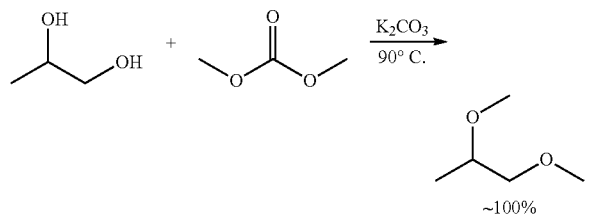

Experimental:

A single neck 100 mL boiling flask equipped with a PTFE-coated magnetic stir bar was charged with 1 g of propylene glycol (PG, 13.1 mmol), 7.27 g of potassium carbonate (52.6 mmol), and 50 mL of dimethyl carbonate. A water cooled Friedrichs condenser was outfitted to the boiling flask and the mixture then heated to 90° C. overnight. After this time, an aliquot was removed, filtered, and analyzed by GC/MS, which revealed that all the PG had been converted to the dimethyl ether analog, with no evidence of monomethyl ether products.

Example 4: EG Methyl Etherification in Methanol

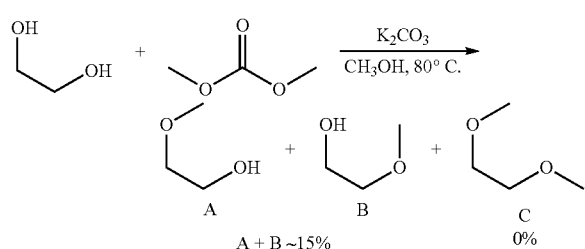

Experimental:

A 100 mL boiling flask was charged with 1 g of ethylene glycol (EG, 16.1 mmol), 1.35 mL of dimethyl carbonate (16.1 mmol), 11.13 g of potassium carbonate (52.6 mmol), and 40 mL of methanol. The mixture was equipped with a Freidrichs condenser and refluxed (~80° C.) overnight. After this time, the heterogeneous mixture was cooled to room temperature, excess potassium carbonate filtered, and filtrate stored. A sample of the filtrate was quantitatively analyzed by GC/MS, the results of which indicated that approximately 15% of EG had converted evenly to the corresponding mono-methyl ethers A and B. Neither the EG dimethyl ether nor other products were observed.

Example 5: EG Methyl Etherification, Neat

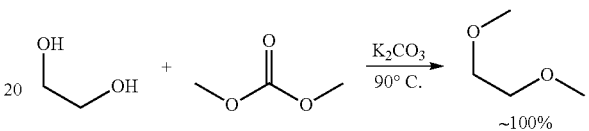

Experimental:

A single neck 100 mL boiling flask equipped with a PTFE coated magnetic stir bar was charged with 1 g of ethylene glycol (EG, 16.1 mmol), 11.13 g of potassium carbonate (52.6 mmol), and 50 mL of dimethyl carbonate. A water cooled Friedrichs condenser was outfitted to the boiling flask and the mixture then heated to 90° C. overnight. After this time, an aliquot was removed, filtered, and analyzed by GC/MS, which revealed that all the EG had been converted to the dimethyl ether analog with no indication of monomethyl ether products.

Example 6: EG Methyl Etherification in Methanol (1:1 EG/DMC)

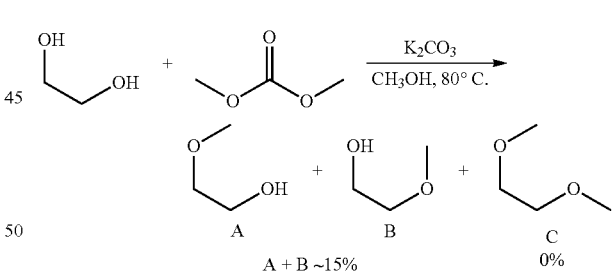

Experimental:

A 100 mL boiling flask was charged with 1 g of ethylene glycol (EG, 16.1 mmol), 1.35 mL of dimethyl carbonate (16.1 mmol), 11.13 g of potassium carbonate (52.6 mmol), and 40 mL of methanol. The mixture was equipped with a Freidrichs condenser and refluxed (~80° C.) overnight. After this time, the heterogeneous mixture was cooled to room temperature, excess potassium carbonate filtered, and filtrate stored. A sample of the filtrate was quantitatively analyzed by GC/MS, the results of which indicated that approximately 15% of EG had converted evenly to the corresponding mono-methyl ethers A and B. Neither the EG dimethyl ether nor other products were observed.

C. Linear Alkylene Glycol Carbonates

Example 7: Synthesis of Diphenyl Propane-1,2-Diyl Dicarbonate, PG Diphenylcarbonate C

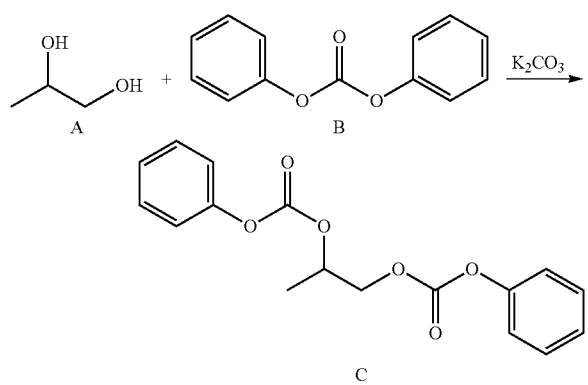

Experimental:

A 25 mL round bottomed flask equipped with an oval PTFE magnetic stir bar was charged with 1 g of propylene glycol A (13.1 mmol), 5.65 g of diphenylcarbonate B (25.2 mmol), and 3.65 g of potassium carbonate (25.2 mmol). While stirring and under an argon blanket, the heterogeneous mixture was heated to 100° C. overnight. After this time, the mixture was dilute with 20 mL of methylene chloride, filtered to removed excess solids, and analyzed by TLC (2% methanol in ethyl acetate, UV-Vis and potassium permanganate illumination), which indicated that all the propylene glycol had been consumed and furthermore indicated only 1 spot. An aliquot of the mother liquor was removed, diluted with $CDCl_3$, and analyzed by NMR. $^1$H NMR ($CDCl_3$, 400 MHz) δ (ppm) 7.29-7.27 (m, 4H), 7.17-7.15 (m, 4H), 7.13-7.11, 4.70-4.69 (m, 1H), 4.10-4.08 (m, 1H), 4.01-3.99 (m, 1H), 1.47 (s, 3H); $^{13}$C NMR ($CDCl_3$, 125 MHz) δ (ppm) 158.54, 157.51, 153.38, 151.15, 129.78, 126.16, 121.32, 116.14, 114.65, 74.05, 73.02, 16.55.

D. Furanic Diol (FDM & bHMTHF) Ethers

Example 1. Synthesis of (5-(Methoxymethyl)Furan-2-Yl)Methanol B, 2,5-Bis(Methoxymethyl)Furan C

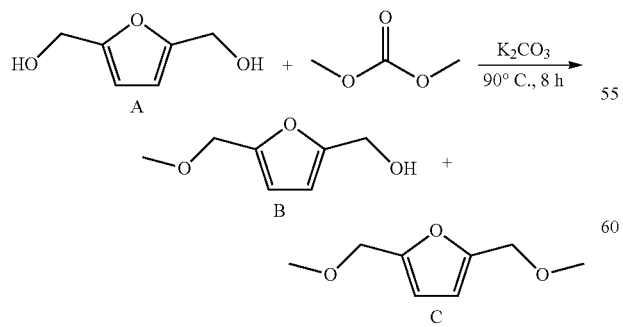

Experimental:

A 10 mL single neck boiling flask equipped with a PTFE coated magnetic stir bar was charged with 100 mg of A (FDM, 0.780 mmol), 539 mg of potassium carbonate (3.902 mmol), and 5 mL of dimethyl carbonate (413 mmol). A reflux condenser was fitted to the flask, and while stirring, the heterogeneous mixture was heated to 90° C. for 8 hours. After this time, the residual potassium carbonate was removed by filtration, and the filtrate concentrated under reduced pressure. The resulting light yellow oil was dissolved in a minimum amount of methylene chloride and charged to pre-fabricated silica gel column, where flash chromatography with ethyl acetate furnished two sets of fractions: A) Those comprising C as a translucent oil, $R_f$=0.72, weighing 26 mg after concentration. Elemental analysis of this material revealed the following results: Expected for $C_8H_{12}O_3$, C, 61.52; H, 7.74. Found C, 61.43; H, 7.85. B) Those representing B as a waxy beige solid, $R_f$=0.54, weighing 21 mg after concentration. Elemental analysis of this substance disclosed the following results: Expected for $C_7H_{10}O_3$, C, 59.15; H, 7.09. Found C, 59.28; H, 7.07.

Example 2: Synthesis of ((2S,5R)-5-(methoxymethyl)tetrahydrofuran-2-yl)methanol, ((2S,5S)-5-(methoxymethyl)tetrahydrofuran-2-yl)methanol, ((2R,5R)-5-(methoxymethyl)tetrahydrofuran-2-yl)methanol B; (2R,5S)-2,5-bis(methoxymethyl)tetrahydrofuran, (2S,5S)-2,5-bis(methoxy-methyl)tetrahydrofuran, C

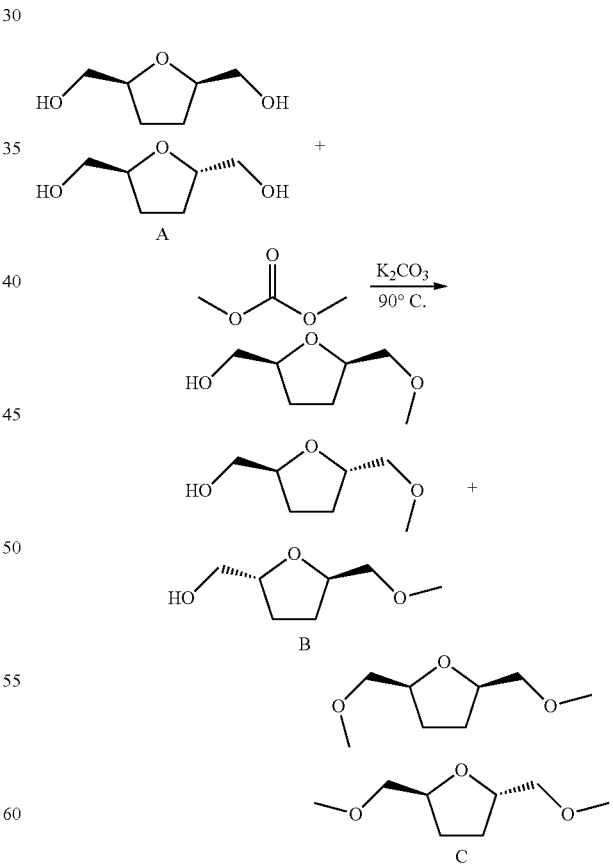

Experimental:

A single neck, 25 mL round bottomed flask equipped with a PTFE coated magnetic stir bar was charged with 250 mg of A (9:1 cis/trans, 1.89 mmol), 1.05 g of potassium carbonate (7.57 mmol), and 15 mL of dimethyl carbonate. A reflux condenser was fitted to the flask, and while stirring, the heterogeneous mixture was heated to 90° C. for 12 h. After this time, the pale yellow residue was concentrated under reduced pressure, furnishing a loose, transparent oil. This oil was then dissolved in a minimum amount of methylene chloride and charged to a pre-fabricated silica gel column, where flash chromatography with an ethyl acetate eluent furnished two sets of fractions: A) Those constituting C, (Rf=0.67, 68 mg of a loose, colorless oil after concentration) that disclosed the following elemental analysis results: Expected for $C_8H_{16}O_3$, C, 59.98; H, 10.07. Found: C, 59.87; H, 10.01. B) Those comprising B, (Rf=0.46, 94 mg of a loose colorless oil after concentration) that revealed the following elemental analysis results: Expected for $C_7H_{14}O_3$, C, 57.51; H, 9.65. Found C, 57.70, H, 9.53.

E. Furanic Diol Carbonates

Example 1. (5-(hydroxymethyl)furan-2-yl)methyl propyl carbonate B, furan-2,5-diylbis(methylene) dipropyl bis(carbonate) C

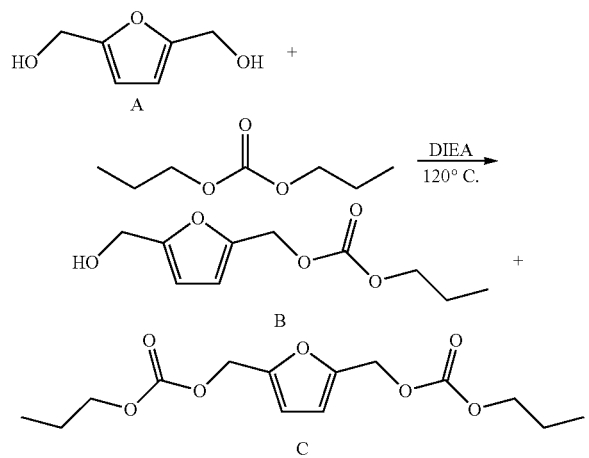

Experimental:

A single neck, 5 mL round bottomed flask equipped with a PTFE coated magnetic stir bar was charged with 100 mg of A (0.780 mmol), 1.21 mL dipropylcarbonate (DPC, 7.80 mmol), and 543 μL DIEA (3.12 mmol). The neck was stoppered with a rubber septum affixed to an argon inlet and the mixture heated to 120° C. overnight under an argon blanket with vigorous stirring. After this time, excess DPC and DIEA were removed under high vacuum, and the mixture dissolved in a 1 mL of methylene chloride and charged to a pre-fabricated silica gel column, where flash chromatography with hexanes/ethyl acetate eluent gradient furnished fractions particular to C ($Rf_1$=0.72) weighing 22 mg, as a tacky, translucent semi-solid after concentration. $^1$H NMR analysis (400 MHz, $CDCl_3$) revealed the following signals δ (ppm): 6.23 (d, J=8.2 Hz, 1H), 6.15 (d, J=8.2 Hz, 1H), 5.21 (s, 2H), 5.10 (t, J=6.8 Hz, 1H), 4.24 (d, J=6.2 Hz, 2H), 4.10 (t, J=7.4 Hz, 2H), 1.59 (m, 2H), 1.10 (t, J=7.0 Hz, 3H). Additionally, eluent fractions particular to B (Rf=0.54) were isolated, affording 28 mg of a loose, colorless oil after inspissation. $^1$H NMR analysis of the mixture revealed the following signals δ (ppm): 6.25 (s, 2H), 5.20 (s, 2H), 4.22 (d, J=6.2 Hz, 2H), 1.61 (m, 2H), 1.03 (t, J=6.8 Hz, 3H).

Example 2: Synthesis of ((2R,5S)-5-(hydroxymethyl)tetrahydrofuran-2-yl)methyl propyl carbonate, ((2S,5S)-5-(hydroxymethyl)tetrahydrofuran-2-yl) methyl propyl carbonate, ((2R,5R)-5-(hydroxymethyl)tetrahydrofuran-2-yl)methyl propyl carbonate B; dipropyl (((2R,5S)-tetrahydrofuran-2,5-diyl)bis (methylene)) bis(carbonate), dipropyl (((2S,5S)-tetrahydrofuran-2,5-diyl)bis(methylene)) bis(carbonate) C

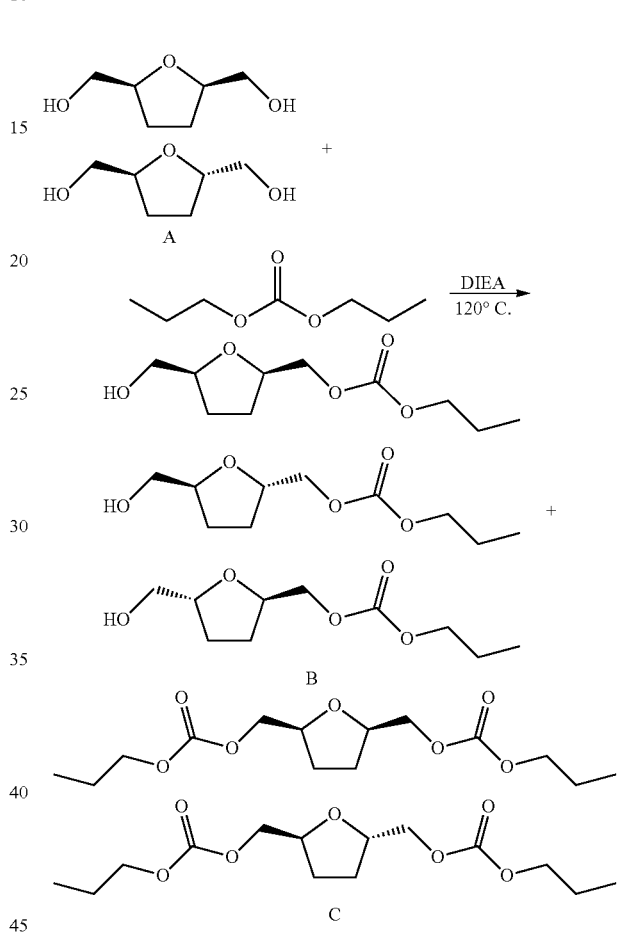

Experimental:

A single neck, 5 mL round bottomed flask equipped with a PTFE coated magnetic stir bar was charged with 100 mg of A (0.751 mmol), 1.17 mL dipropylcarbonate (DPC, 7.51 mmol), and 522 μL DIEA (3.00 mmol). The neck was stoppered with a rubber septum affixed to an argon inlet and the mixture heated to 120° C. overnight under an argon blanket with vigorous stirring. After this time, excess DPC and DIEA were removed under high vacuum, and the tacky, yellow oil dissolved in a minimum amount of methylene chloride, and charged to a pre-fabricated silica gel column. Flash chromatography with ethyl acetate as the eluent afforded two sets of fractions: A) A colorless, loose oil, $R_f$=0.70, weighing 18 mg after concentration that was analyzed by elemental analysis: Expected for $C_{14}H_{24}O_7$, C, 55.25; H, 7.95. Found C, 55.12, H, 7.84. B) A colorless, loose oil, $R_f$=0.52, weighing 26 mg after concentration: Expected for $C_{10}H_{18}O_5$, C, 55.03; H, 8.31. Found C, 55.16, H, 8.24.

The present invention has been described in general and in detail by way of examples. Persons of skill in the art understand that the invention is not limited necessarily to the embodiments specifically disclosed, but that modifications and variations may be made without departing from the scope of the invention as defined by the following claims or their equivalents, including other equivalent components presently know or to be developed, which may be used within the scope of the invention. Therefore, unless changes otherwise depart from the scope of the invention, the changes should be construed as being included herein.

We claim:

1. A method of preparing a mono-ester-ether from a linear or mono-cyclic diol compound, comprising either a first pathway or second pathway, wherein:
   in the first pathway, a diol compound selected from the group consisting of ethylene glycol (EG), propylene glycol (PG), 2,3 butane diol (BDO), furandimethanol and tetrahydrofuran dimethanol is contacted with an $R^1$ organic acid of the formula $R^1$—$CO_2H$ wherein $R^1$ is a $C_1$ to $C_8$ alkyl, cycloalkyl or aromatic moiety in the presence of a Brønsted acid at a temperature and for time sufficient to form a $R^1$ mono ester of the diol compound, then the $R^1$ mono ester of the diol compound is contacted with a $R^2$ alkyl diester of the formula $R^2(CO_3)R^2$ in which $R^2$ is a $C_1$ to $C_8$ alkyl moiety in the presence of a deprotonating agent at a temperature and for a time sufficient to form the monoester ether; or
   in the second pathway, a diol compound selected from the group consisting of ethylene glycol (EG), propylene glycol (PG), 2,3 butane diol (BDO), furandimethanol and tetrahydrofuran dimethanol is contacted with the an $R^2$ alkyl diester of the formula $R^2(CO_3)R^2$ in which $R^2$ is a C1 to C8 alkyl moiety in the presence of a deprotonating agent at a temperature and for a time sufficient to form a mono ether of the diol compound, then the mono ether of the diol compound is contacted with an $R^1$ organic acid of the formula $R^1$—$CO_2H$ wherein $R^1$ is a $C_1$ to $C_8$ alkyl, cycloalkyl or aromatic moiety in the presence of a Brønsted acid at a temperature and for time sufficient to form the monoester ether.

2. The method according to claim 1, wherein said $R^1$ organic acid is acetic acid and said mono-ester-ether is an ether acetate compound.

3. The method according to claim 1, wherein said deprotonating agent is a Brønsted base.

4. The method according to claim 1, wherein said deprotonating agent is selected from the group consisting of potassium carbonate, sodium carbonate, calcium carbonate, and an amine.

5. The method according to claim 1, wherein said temperature for contacting with the Brønsted acid and with the deprotonating agent is at a temperature between about 70° C. and 150° C.

6. The method according to claim 1, wherein said temperature for contacting with the Brønsted acid and with the deprotonating agent is at a temperature between about 80° C. and 130° C.

7. The method according to claim 1 wherein said temperature for contacting with the Brønsted acid and with the deprotonating agent is at a temperature between about 90° C. to about 120° C.

8. The method according to claim 1, wherein said deprotonating agent is an inorganic carbonate present in an amount of at least one (1) to about three (3) stoichiometric equivalents per diol compound.

* * * * *